(12) United States Patent
Sumi et al.

(10) Patent No.: US 6,604,623 B2
(45) Date of Patent: Aug. 12, 2003

(54) ARTICLE TRANSFER APPARATUS

(75) Inventors: Isamu Sumi, Osaka (JP); Yuzo Ichiura, Osaka (JP); Hiromi Mae, Osaka (JP)

(73) Assignee: Zuiko Corporation, Osaka (JP)

( * ) Notice: Subject to any disclaimer, the term of this patent is extended or adjusted under 35 U.S.C. 154(b) by 24 days.

(21) Appl. No.: 10/055,145

(22) Filed: Jan. 23, 2002

(65) Prior Publication Data
US 2002/0112939 A1 Aug. 22, 2002

(30) Foreign Application Priority Data
Jan. 31, 2001 (JP) .................................... 2001-024130

(51) Int. Cl.[7] .............................................. B65G 47/24
(52) U.S. Cl. .............................. 198/377.08; 198/803.5; 294/64.1; 271/196; 271/276
(58) Field of Search ...................... 198/377.08, 468.4, 198/471.1, 750.12, 803.5; 271/94, 96, 196, 276; 414/752.1; 294/64.1

(56) References Cited

U.S. PATENT DOCUMENTS

| | | | | | |
|---|---|---|---|---|---|
| 3,096,977 | A | * | 7/1963 | Winkler et al. | 271/276 |
| 3,689,065 | A | * | 9/1972 | Foret et al. | 271/196 |
| 4,394,898 | A | * | 7/1983 | Campbell | 271/196 |
| 6,116,317 | A | * | 9/2000 | Tharpe et al. | 198/377.08 |
| 6,139,004 | A | * | 10/2000 | Couillard et al. | 271/196 |
| 6,325,201 | B1 | * | 12/2001 | Bailey et al. | 198/471.1 |
| 6,336,492 | B1 | * | 1/2002 | Nagaoka | 294/64.1 |

* cited by examiner

Primary Examiner—Joseph E. Valenza
(74) Attorney, Agent, or Firm—Renner, Otto, Boisselle & Sklar (57) ABSTRACT

With an article transfer apparatus 1 of the present invention, when a negative pressure is applied on an air outlet 20 in a non-attracting state, the amount of air that is sucked through suction holes 6 in a front attracting section 2f is greater than the amount of air that is sucked through suction holes 7 in a rear attracting section 2b. Therefore, the suction amount through the front attracting section 2f is increased while reducing the suction loss of the attracting pad 2, thereby improving the reliability of the attraction operation.

21 Claims, 7 Drawing Sheets

ARTICLE TRANSFER APPARATUS

BACKGROUND OF THE INVENTION

1. Field of the Invention

The present invention relates to a transfer apparatus primarily for transferring an article which is worn such as a disposable diaper or a sanitary napkin.

2. Description of the Related Art

In order to transfer an article of this type from another apparatus in a preceding stage, typically a negative pressure is created using air so as to attract the article onto an attracting pad (e.g., Japanese Laid-Open Patent Publication No. 63-317576).

The attracting pad attracts a front portion of the article and then attracts a rear portion of the article. The present inventors have noticed that all of the suction holes of the attracting pad are open when attracting the front portion of the article, whereby there is a suction loss if one attempts to obtain a sufficient attracting force. The present inventors have also noticed that when attracting the rear portion of the article, since some of the suction holes are already covered by the article, the attracting force may be excessive, which may result in wrinkles in the article.

SUMMARY OF THE INVENTION

An article transfer apparatus is provided which is capable of reliably attracting the article with a sufficient attracting force and yet has a reduced suction loss.

The present invention provides a transfer apparatus, including: an attracting pad including a front attracting section and a rear attracting section each having suction holes for applying a negative pressure, which is created through suction of air, on an article; and a moving section for moving the attracting pad, whereby the attracting pad attracts a front portion of the article by air and then attracts a rear portion of the article by air so as to pick up the article from another apparatus in a preceding stage and to transfer the article that has been picked up, wherein an air suction amount (the amount of air that is sucked) through the front attracting section is set to be greater than an air suction amount through the rear attracting section when a negative pressure is applied on the suction holes in a non-attracting state where the attracting pad is not attracting the article.

When the pad attracts the front portion of the article, the suction holes of the front and rear attracting sections are open, whereby the suction through the rear attracting section is a loss. However, the suction loss is reduced because the suction amount through the rear attracting section is smaller than the suction amount through the front attracting section. Moreover, since the suction amount through the front attracting section is greater, and thus the attracting force thereof is greater, the reliability of the attraction operation is improved in the beginning of the operation of attracting the article.

On the other hand, after the front portion of the article has been attracted, since the suction holes of the front attracting section are covered by the article, the attraction of the article increases the suction amount through the rear attracting section relative to the suction amount through the front attracting section, whereby a sufficient attracting force can be obtained also in the rear attracting section.

Herein, the term "suction hole" may refer to a hole opened in the attracting surface of the attracting pad, or an equivalent thereof.

The term "front attracting section" may refer to a section that attracts the article first or earlier than another section, or an equivalent thereof, and "rear attracting section" may refer to a section that attracts the article last or later than another section, or an equivalent thereof.

Herein, the phrase "the suction amount through the front attracting section is set to be greater than the suction amount through the rear attracting section" may mean that the air suction resistance through the front attracting section is set to be smaller than the air suction resistance through the rear attracting section when a negative pressure is applied on the suction holes in a non-attracting state where the attracting pad is not attracting the article.

The air suction resistance through the front attracting section (rear attracting section) decreases as the number and the area (cross-sectional area) of the suction holes provided in the front attracting section (rear attracting section) increase, and increases as the length of each suction hole increases.

A specific method of setting the suction amounts as described above is to set the total cross-sectional area of the suction holes of the front attracting section to be greater than that of the rear attracting section.

Herein, the term "cross-sectional area of a suction hole" may refer to the area of the suction hole along a cross section thereof that is perpendicular to the axial line of the suction hole, and it generally coincides with the area of the opening of the suction hole on the attracting surface of the pad. However, when the axial line of the suction hole is not perpendicular to the attracting surface, the cross-sectional area of the suction hole is smaller than the area of the opening thereof. Moreover, when the suction hole is tapered so as to expand in the vicinity of the attracting surface, the cross-sectional area of the suction hole is smaller than the area of the opening thereof.

It is typically preferred that the cross-sectional shape of a suction hole is a circular shape. However, it may alternatively be an elliptical shape, a rectangular shape, a polygonal shape, or the like. It may even be an oval shape or a slit-like shape (groove-like shape). Moreover, while it is typically preferred that the number of suction holes is more than one, it may alternatively be one if the suction hole has a slit-like shape.

In a case where a plurality of suction holes are provided in each of the front and rear attracting sections, it is typically preferred that the number of suction holes in the front attracting section is greater than the number of suction holes in the rear attracting section. However, the same number of suction holes may alternatively be provided in the front attracting section and in the rear attracting section.

Based on the above, the suction amount through the front attracting section can be set to be greater than the suction amount through the rear attracting section in one of the following manners, for example:

(1) Provide the same number of suction holes in the front attracting section and in the rear attracting section, with the cross-sectional area of the suction holes in the front attracting section being greater than that in the rear attracting section;

(2) Set the cross-sectional area of the suction holes in the front attracting section to be substantially the same as that in the rear attracting section, with the number of suction holes in the front attracting section being greater than that in the rear attracting section;

(3) Set the number and the cross-sectional area of the suction holes in the front attracting section to be greater than those in the rear attracting section; and (4) Set the cross-sectional area of the air suction path communicated to the suction holes in the front attracting section to be greater than that in the rear attracting section. The air suction resistance can be adjusted by providing an orifice along the air suction path.

Herein, the term "article" may refer primarily to a worn article. Herein, the term "worn article" is a concept encompassing a multilayer material made of at least one of a nonwoven, a fabric and a fiber, a single layer fabric or nonwoven, and the like, including a finished or semi-finished product of a sanitary napkin, a disposable diaper, or disposable pants. Herein, the term "nonwoven" includes staple nonwoven, filament nonwoven, wetlaid nonwoven, drylaid nonwoven, airlaid nonwoven, airlaid pulp nonwoven, carded nonwoven, parallel-laid nonwoven, cross-laid nonwoven, randomlaid nonwoven, spunlaid nonwoven, meltblown nonwoven, and the like. Methods for manufacturing a disposable worn article while changing the interval between semi-finished products of the disposable worn article are disclosed in, for example, Japanese Laid-Open Patent Publication No. 64-38377, Japanese Laid-Open Patent Publication No. 3-176053, Japanese Laid-Open Patent Publication No. 4-161152, and U.S. Pat. No. 5,660,657, which are incorporated herein by reference.

In a case where the orientation of pads changes, the interval between the pads transferring semi-finished products thereon also changes.

DESCRIPTION OF THE PREFERRED EMBODIMENTS

The present invention will be more fully understood from the following description of a preferred embodiment thereof with reference to the accompanying drawings. Throughout the views of the drawings, like reference numerals denote like elements.

A preferred embodiment of the present invention will now be described with reference to the drawings.

Figure 1A:
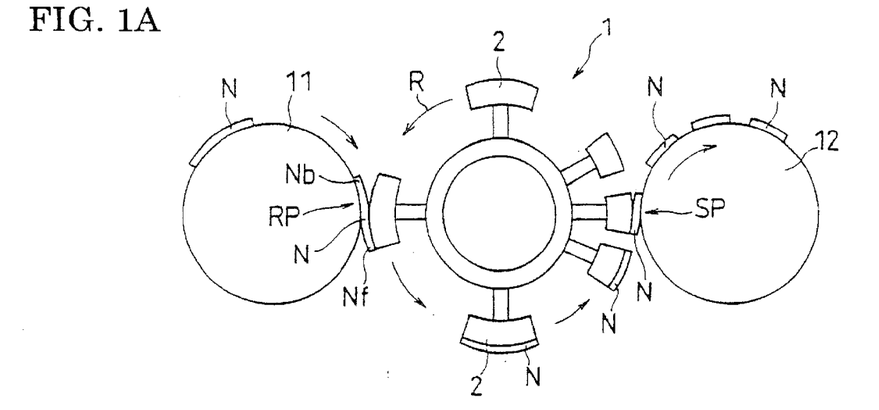
FIG. 1A is a schematic layout diagram illustrating an example of a transfer device according to the present invention.
Figure 2:
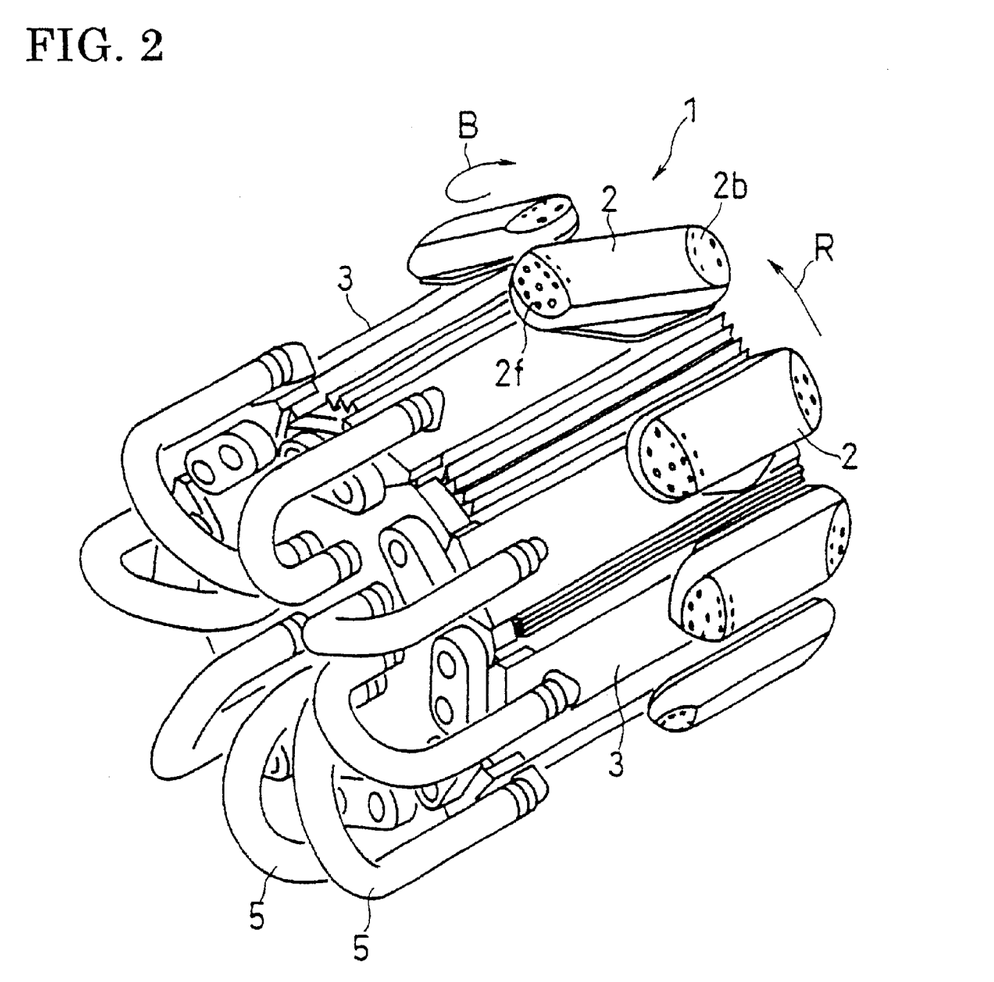
FIG. 2 is a schematic perspective view illustrating one embodiment of a transfer apparatus.

As illustrated in FIG. 1A, a transfer apparatus 1 picks up worn articles N at a pickup position RP from an upstream first roll (apparatus in the preceding stage) 11, changes the interval between the worn articles N. and transfers the worn articles N to a hand-over position SP, at which the worn articles N are handed over to a downstream second roll (apparatus in the subsequent stage) 12. As illustrated in FIG. 2, the transfer apparatus 1 includes a plurality of attracting pads 2 around a drum (not shown). The interval between the attracting pads 2 is changed while the attracting pads 2 move from the pickup position RP to the hand-over position SP. Mechanisms for performing such a re-pitching operation are disclosed in, for example, Japanese Laid-Open Patent Publication No. 63-317576, International Publication WO01/44086, U.S. Pat. No. 6,022,443, and U.S. Pat. No. 4,610,751, which are incorporated herein by reference. The attracting pad 2 is rotated by a known moving section (not shown) in the direction indicated by arrow R together with a base 3 while revolving on the base 3 as indicated by arrow B to change the orientation of the worn article N by about 90°. The orientation changing section for changing the orientation of the worn articles N may be a cam groove as disclosed in Japanese Laid-Open Patent Publication No. 63-317576 or International Publication WO01/44086, for example.

Note that the first and second rolls 11 and 12 can attract the worn articles N by an application of negative air pressure.

The moving section changes the interval between the attracting pads 2, 2 while moving the attracting pads 2 from the pickup position RP to the hand-over position SP shown in FIG. 1A. In the present invention, it is not necessary that the moving section change the interval between the attracting pads 2, 2. Moreover, in the present invention, it is not necessary that the moving section change the orientation of the attracting pads 2. Furthermore, the attracting pads 2 may be moved in the circumferential direction while shifted with respect to one another in a direction transversal to the direction in which the attracting pads 2 are moved. For the structure of the moving section of this type, Japanese Laid-Open Patent Publication No. 63-317576 and Japanese National Phase PCT Laid-Open Publication No. 2000-514024 are incorporated herein by reference.

It is typically preferred that the circumferential velocity of the first roll 11 at the pickup position RP is set to be substantially the same as that of the transfer apparatus 1. For example, while a plurality of attracting pads 2 are shown in FIG. 1A, each attracting pad 2 can move at an independent velocity. Since each attracting pad 2 can move at any velocity, the interval between the attracting pads 2, 2 can be changed.

Figure 1B:
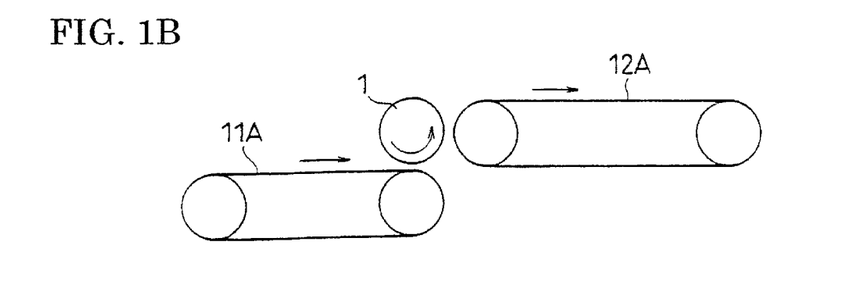
FIG. 1B is a schematic layout diagram illustrating an example of a transfer device according to the present invention.

The apparatus in the preceding stage and the apparatus in the subsequent stage may be a first conveyer 11A and a second conveyer 12A, respectively, as illustrated in FIG. 1B. Alternatively, the apparatus in the subsequent stage may be the second conveyer 12A as illustrated in FIG. 1D. Alternatively, the apparatus in the preceding stage may be a first conveyer (not shown). These conveyers may attract the worn articles N through suction. In such a case, each conveyer includes a plurality of holes.

Figure 1C:
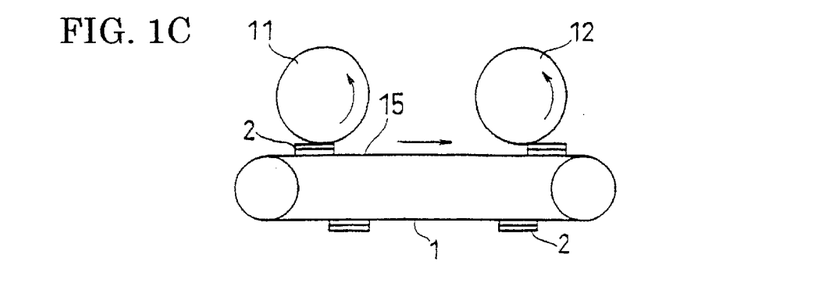
FIG. 1C is a schematic layout diagram illustrating an example of a transfer device according to the present invention.
Figure 1D:
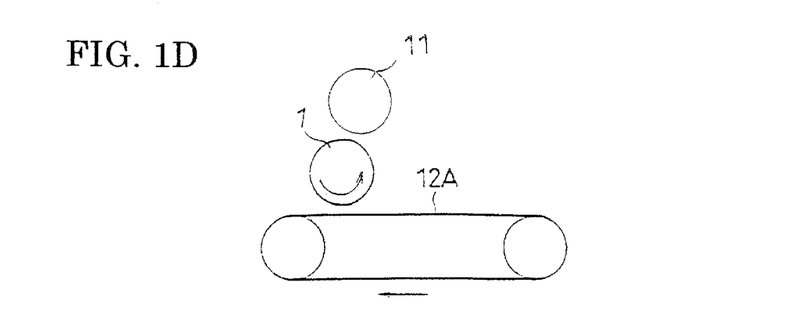
FIG. 1D is a schematic layout diagram illustrating an example of a transfer device according to the present invention.

The transfer apparatus 1 may alternatively be an endless conveyer 15, as illustrated in FIG. 1C, instead of a drumshaped apparatus. The conveyer 15 is provided with a plurality of attracting pads 2. Each attracting pad 2 can move on the conveyer 15 at an independent velocity, so that the velocity of the attracting pad 2 picking up the worn article N is substantially the same as the circumferential velocity of the first roll while the velocity of the attracting pad 2 handing over the worn article N is substantially the same as the circumferential velocity of the second roll. Such independent velocity may be achieved, for example, via linear motors (not shown) designed to control electromagnets (also not shown) on the back side of the conveyer 15. The movement of the electromagnets provide independent velocity control of the attracting pads 2 which are respectively attracted thereto. In FIG. 1C, each attracting pad 2 has a flat surface in at least one of the pickup position and the hand-over position.

As illustrated in FIG. 2, the transfer apparatus 1 includes a plurality of vacuum hoses 5, via which the air is sucked out through the attracting pads 2, as will be described later.

Figure 3A:
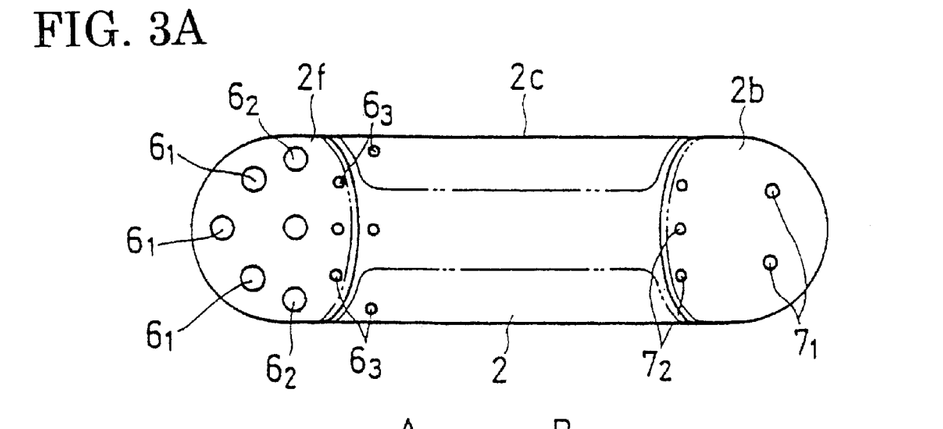
FIG. 3A is a plan view illustrating an example of an attracting pad.
Figure 3B:
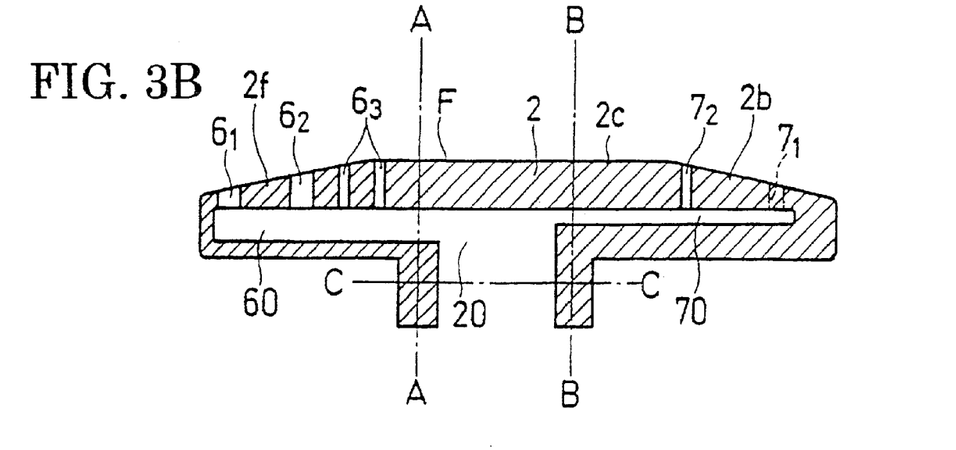
FIG. 3B is a vertical cross-sectional view illustrating the attracting pad of FIG. 3A.
Figure 4:
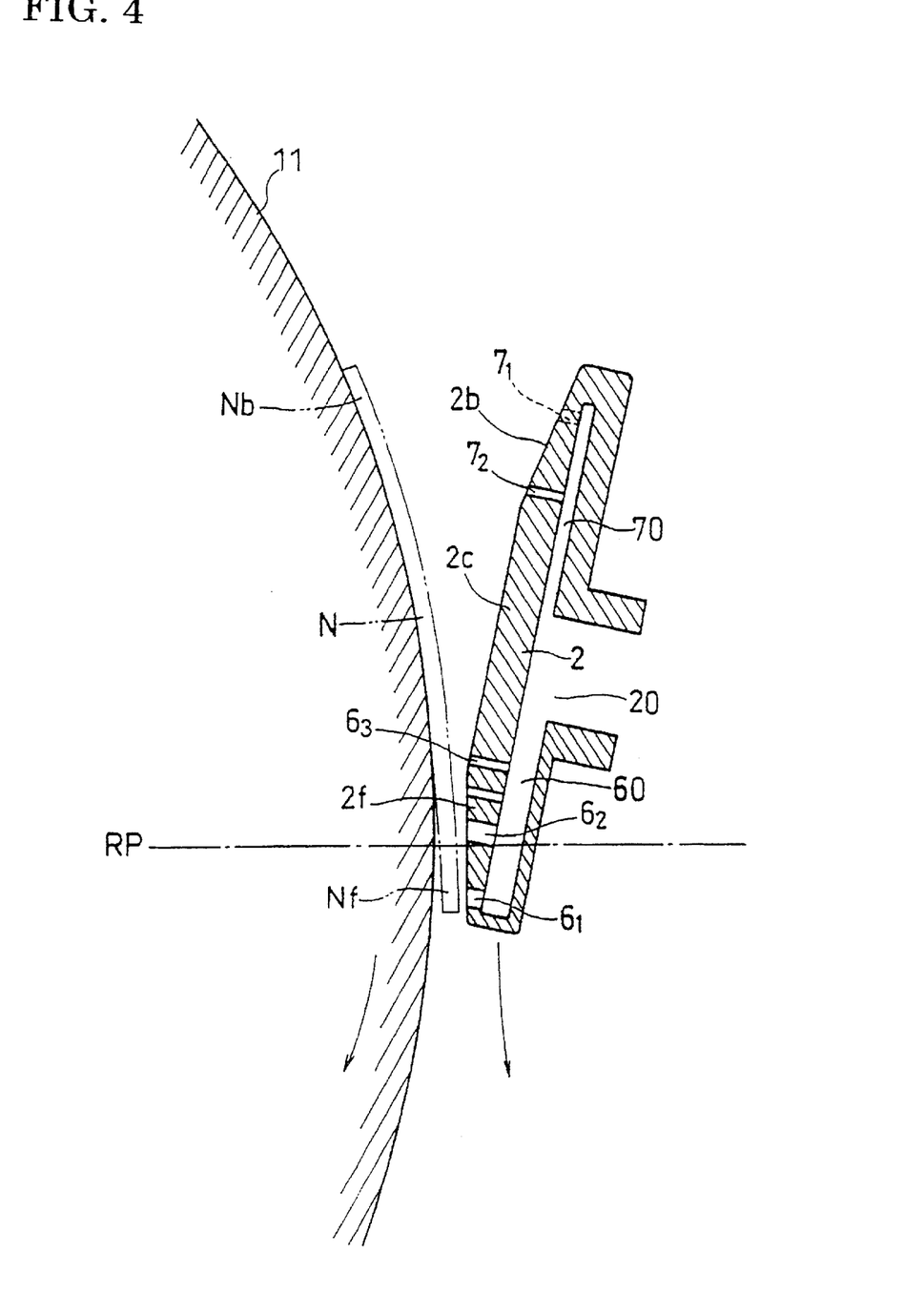
FIG. 4 is a cross-sectional view illustrating an important part immediately before an attraction operation at a pickup position.
Figure 5:
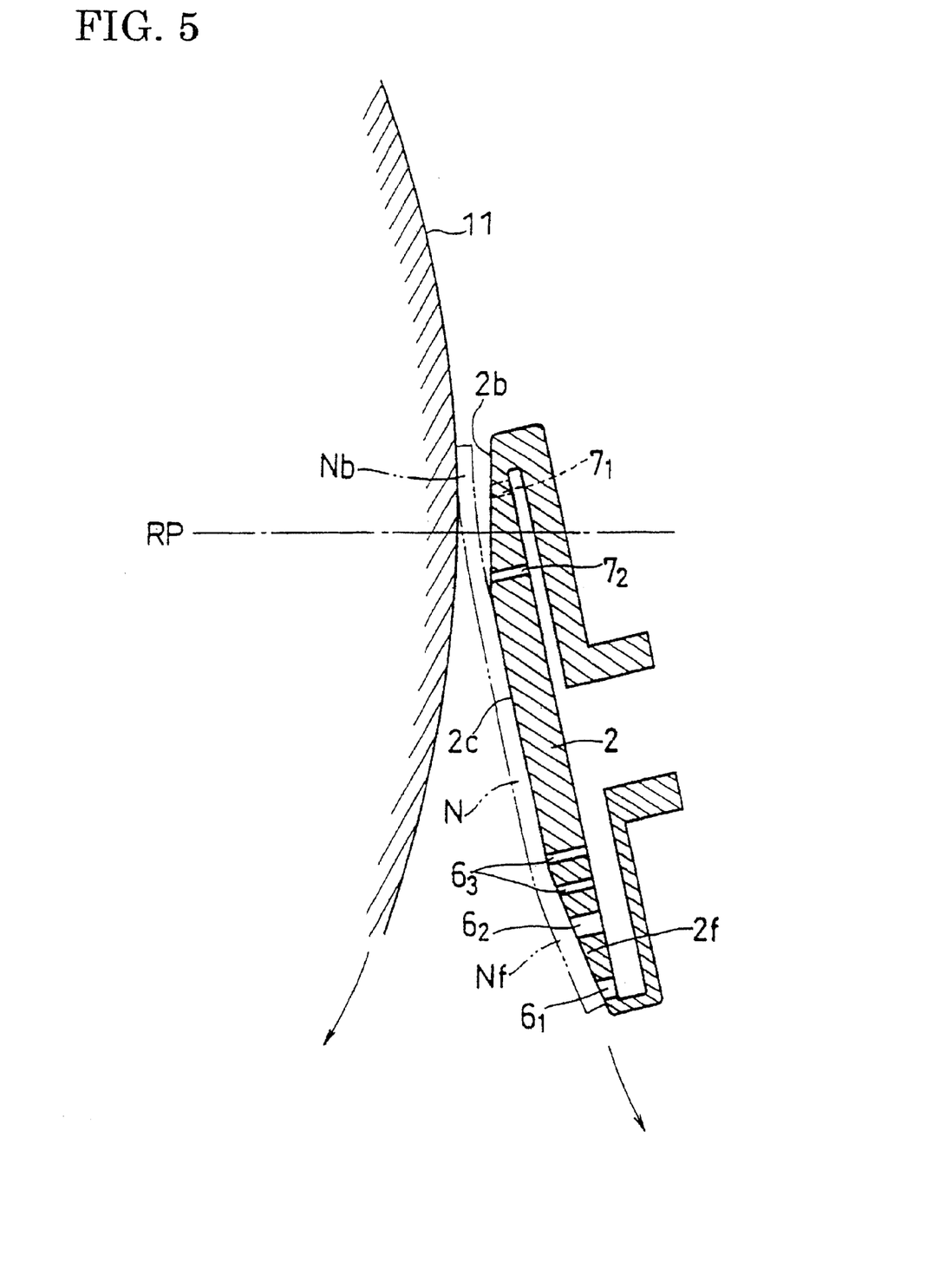
FIG. 5 is a cross-sectional view illustrating an important part during the attraction operation.

As illustrated in FIG. 3A and FIG. 3B, each attracting pad 2 includes a front attracting section $2f$ and a rear attracting section $2b$. In the present embodiment, the attracting pad 2 further includes a central portion $2c$ between the front attracting section $2f$ and the rear attracting section $2b$. As illustrated in FIG. 4 and FIG. 5, at the pickup position RP, the front attracting section $2f$ of the attracting pad 2 attracts a front portion Nf of the worn article N, and then the worn article N is pulled onto the central portion $2c$, after which the rear attracting section $2b$ attracts a rear portion Nb of the worn article N as illustrated in FIG. 5. Note that at least one of the pickup position RP and the hand-over position SP may have a predetermined width.

As illustrated in FIG. 3A, the front attracting section $2f$ and the rear attracting section $2b$ of each attracting pad 2 include many suction holes $6_i$ and $7_i$, respectively, which are opened in a surface F thereof. The suction holes $6_i$ and $7_i$ are communicated to a negative pressure source (not shown) via at least one front path 60 and at least one rear path 70, respectively. Specifically, the front path 60 is communicated primarily to the suction holes in the front attracting section $2f$, while the rear path 70 is communicated primarily to the suction holes in the rear attracting section $2b$. The front path 60 and the rear path 70 are communicated to an air outlet 20. The air outlet 20 may be located in a side of the front attracting section $2f$. In such a case, the rear path 70 may be communicated to the air outlet 20 via at least one front path 60 or a part of the front path 60.

Figure 3C:
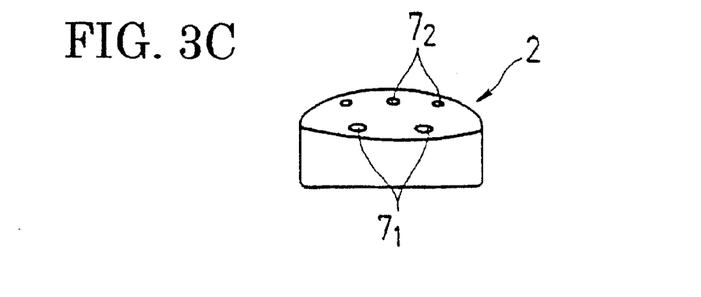
FIG. 3C is a side view illustrating the attracting pad of FIG. 3A.

Each end portion of each attracting pad 2 is cut into a tapered shape, and the attracting pad 2 has a curved surface with the central portion thereof being slightly raised relative to the other portions, as illustrated in FIG. 3C, though this does not limit the shape of the attracting pad 2 of the present invention. It is preferred, however, that the attracting pad 2 contacts the first roll, or the like, for picking up the worn article N. Therefore, it is preferred that the surface of the attracting pad 2 has a shape such that it contacts the first roll, or the like, at the pickup position RP, with the distance from the center of rotation of the transfer apparatus 1 being constant (Condition 1). Similarly, it is preferred that the attracting pad 2 contacts the second roll, or the like, at the hand-over position SP for handing over the worn article N. Therefore, it is preferred that the surface of the attracting pad 2 has a shape such that it contacts the second roll, or the like, with the distance from the center of rotation of the transfer apparatus 1 being constant (Condition 2). In a case where the attracting pad 2 is revolved so as to change the orientation of the worn article N, it is preferred that the surface of the attracting pad 2 satisfies Conditions 1 and 2. However, in order to prevent the operation of processing the surface of the attracting pad 2 from becoming complicated, only the end portions of the attracting pad 2 may be processed so as to satisfy Conditions 1 and 2. An example of the shape of the edge portion is shown by a two-dot chain line in FIG. 3A. In a case where it is not necessary to pivot the orientation of the worn article N, the surface of the attracting pad 2 may have a shape such that it forms a part of a cylindrical surface about the center of rotation of the transfer apparatus 1.

Figure 7:
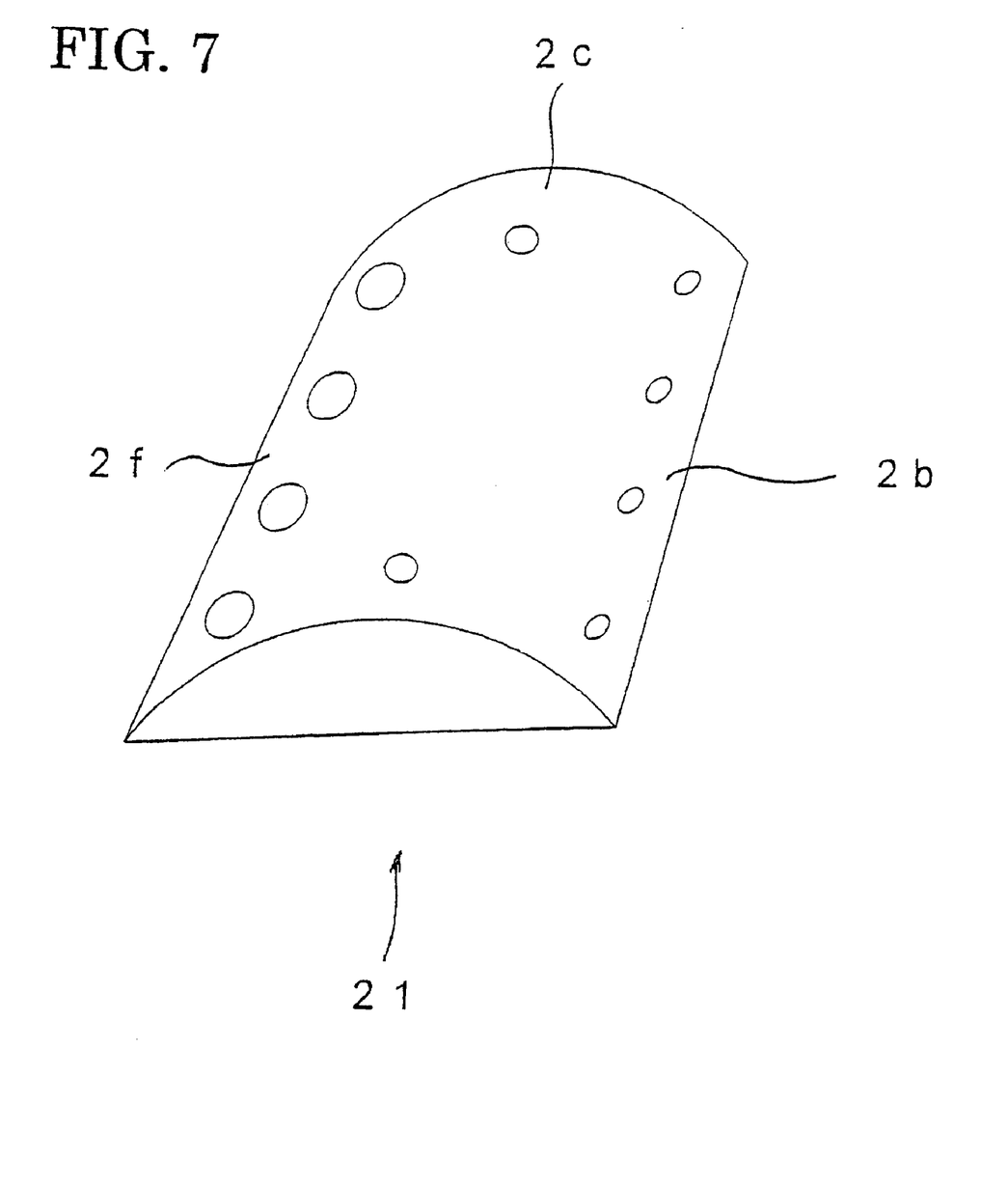
FIG. 7 is a diagram illustrating still another example of an attracting pad.

Alternatively, an attracting pad 21 having a shape which is a portion of a circular column including a part of the side surface thereof, as illustrated in FIG. 7 may be employed. Particularly, in a case where the apparatus in the preceding stage is the first roll 11 and the apparatus in the subsequent stage is the second conveyer 12A, as illustrated in FIG. 1D, the transfer apparatus 1 may suitably employ the attracting pad 21. The attracting pad 21 is preferably employed where the worn article N has a thickness greater than a predetermined thickness, where the worn article N has a size greater than a predetermined size, or where the worn article N has a firmness greater than a predetermined firmness. The worn article N is bent in one direction into a saddle-like shape, conforming to the shape of the attracting pad 21. This is so intended because the worn article N may be wrinkled if it is bent in the opposite direction. Note that the radius of the circumference of the attracting pad 21 may be determined by the distance from the circumference of the first roll 11 to the center of rotation of the transfer apparatus 1 at the pickup position, at which the worn article N is picked up. The attracting pad 21 includes the front attracting section $2f$ and the rear attracting section $2b$. In the present embodiment, the attracting pad 21 further includes the central portion $2c$ between the front attracting section $2f$ and the rear attracting section $2b$.

In the present embodiment as illustrated in FIG. 3A, the front attracting section $2f$ includes a greater number of suction holes than the rear attracting section $2b$. For example, the number of suction holes may gradually decrease along the length of the attracting pad 2 from the front attracting section $2f$ to the rear attracting section $2b$. Moreover, in the present embodiment, the total cross-sectional area of the suction holes $6_i$ of the front attracting section $2f$ is greater than the total cross-sectional area of the suction holes $7_i$ of the rear attracting section $2b$. For example, the total cross-sectional area of the suction holes may gradually decrease along the length of the attracting pad 2 from the front attracting section $2f$ to the rear attracting section $2b$.

Alternatively, the cross-sectional area per unit area of the suction holes $6_i$ in the vicinity of the attracting surface F of the attracting pad 2 may be greater than the cross-sectional area per unit area of the suction holes $7_i$ in the vicinity of the surface F of the attracting pad 2. Note that in a case where each suction hole is tapered as will be described below, the cross-sectional area is measured at a position where the cross-sectional area of the suction hole is at minimum.

Accordingly, if a negative pressure from the negative pressure source is applied on the suction holes $6_1$ and $7_1$ while the attracting pad 2 of FIG. 1A rotates from the hand-over position SP to the pickup position RP without the worn article N being attracted thereonto, the air suction resistance through all suction holes $6_1$ to $6_2$ of the front attracting section $2f$ is smaller than the air suction resistance through all suction holes $7_1$ to $7_2$ of the rear attracting section $2b$. Therefore, under such a condition, the suction amount through the front attracting section $2f$ is greater than that of the rear attracting section $2b$.

The air suction amount through the front attracting section $2f$ in a non-attracting state may be set to be equal to or greater than 1.5 times, or even 2 times, that of the rear attracting section $2b$.

Next, the mechanism by which the worn articles N are transferred by the attracting pads as illustrated in FIG. 3A will be described.

As illustrated in FIG. 4, the first roll 11, which is attracting the worn article N by a negative pressure of air, starts releasing the vacuum at a position before the pickup position RP. On the other hand, as the attracting pad 2 approaches the pickup position RP, the suction holes $6_i$ and $7_i$ are communicated to the negative pressure source. With no worn article N being attracted onto the attracting pad 2, all the suction holes $6_i$ and $7_i$ are open. Therefore, when the front attracting section $2f$ starts attracting the front portion Nf of the worn article N, i.e., in the beginning of the attraction operation, as illustrated in FIG. 4, the suction through the suction holes $7_1$ in the rear attracting section $2b$ is a loss. With the present transfer apparatus, however, the air suction amount through the rear attracting section $2b$ is relatively reduced, thereby reducing the suction loss, while the suction amount through the front attracting section $2f$ is relatively increased, thereby reliably attracting the front portion Nf of the worn article N.

As the first roll 11 and the attracting pad 2 further rotate, the front portion Nf of the worn article N is attracted onto the front attracting section $2f$. Then, the worn article N is pulled onto the surface of the central portion $2c$, and the rear attracting section $2b$ starts attracting the rear portion Nb of the worn article N, as illustrated in FIG. 5.

When the rear attracting section $2b$ starts attracting the worn article N, i.e., during its attraction operation, the suction holes $6_i$ of the front attracting section $2f$ are covered by the worn article N, thus avoiding the possible suction loss therethrough. Therefore, the suction amount is increased even if the air suction resistance through the suction holes $7_i$ in the rear attracting section $2b$ is relatively large.

The attracting pad 2 with the worn article N being attracted thereonto rotates from the pickup position RP to the hand-over position SP, as illustrated in FIG. 1A. Before reaching the hand-over position SP, the communication to the negative pressure source is cut off. Then, air flows into the suction holes $6_1$ and $7_i$ of FIG. 3B through the air outlet 20 or through a large number of pores in the worn article N, thereby weakening the attracting force of the attracting pad 2. In the illustrated example, the front path 60 of the front attracting section $2f$, etc., receives a greater amount of air flowing in from the outside of the attracting pad 2, than the rear path 70 of the rear attracting section $2b$, etc. Accordingly, the air pressure (pressure) of the front path 60, etc., may be slightly higher than the air pressure (pressure) of the rear path 70, etc. Therefore, the attracting force of the rear attracting section $2b$ acting upon the worn article N may be slightly higher than that of the front attracting section $2f$. When the attracting pad 2 reaches the hand-over position SP, the worn article N is picked up by the second roll 12, which attracts the worn article N thereonto. Thus, the attracting pad 2 is capable of attracting the worn article N thereonto until the worn article N is picked up by the second roll 12.

Next, an example of the front path 60 and the rear path 70 of the attracting pad 2 in the present transfer apparatus will be described.

As illustrated in FIG. 3B, the front path 60 is a path that is communicated to the suction holes $6_i$ of the front attracting section $2f$, etc., and the rear path 70 is a path that is communicated to the suction holes $7_1$ of the rear attracting section $2b$, etc. The cross-sectional area "a" of the front path 60 taken along line A—A is greater than the cross-sectional area "b" of the rear path 70 taken along line B—B. Herein, the cross-sectional area "a" refers to the effective total cross-sectional area if there are more than one front paths 60. Being "effective" herein means that it is a cross-sectional area of the front path 60 through which the air can flow from the suction holes $6_i$. This similarly applies to the cross-sectional area "b". Thus, if air is sucked through the air outlet 20 with no worn article N being attracted, the amount of air that is sucked through the front path 60 is greater than the amount of air that is sucked through the rear path 70. Moreover, it is preferred that the cross-sectional area "c" of the air outlet 20 taken along line C—C is greater than the sum of the cross-sectional area "a" of the front path 60 and the cross-sectional area "b" of the rear path 70, so as to ensure sufficient suction, etc.

While FIG. 3B illustrates the front path 60 and the rear path 70 as being simply communicated to the suction holes $6_i$ and $7_i$, respectively, the path pattern from the air outlet 20 to the suction holes $6_i$ and $7_i$ may be a complicated path like a maze. For example, the path from the air outlet 20 to the suction holes $6_i$ $7_i$ may include a straight portion or a curved portion, and a plurality of spaces for adjusting at least one of the air capacity and the air suction resistance may be connected along the path.

It is preferred that the path pattern is designed so that the three suction holes $6_1$ in the front end portion shown in FIG. 3A have substantially the same suction amount. It is also preferred that the pattern of the front path 60 is designed so that when the suction holes $6_1$ in the front end portion have been covered by the worn article N, the three suction holes $6_2$ in the next row have substantially the same suction amount as one another and as the suction holes $6_1$ in the front end portion. This is because the worn article N may be wrinkled if the attracting force of the suction holes $6_1$ is considerably different from the attracting force of the adjacent suction holes $6_2$. In other words, it is preferred that suction holes that suck onto the worn article N substantially simultaneously have substantially the same suction amount. Similarly, it is preferred that the two suction holes $7_1$ in the rear end portion have substantially the same suction amount.

Each suction hole $6_1$ in the front end portion may have a larger diameter than that of a suction hole in the rear end portion. Moreover, the suction holes $6_1$ that first suck onto the worn article N may be provided along the side edge at the front end of the attracting pad 2 so as to reliably attract the worn article N onto the attracting pad 2. Furthermore, the size of the attracting pad 2 may be substantially the same as, or slightly larger or smaller than, that of the worn article N.

Figure 6A:
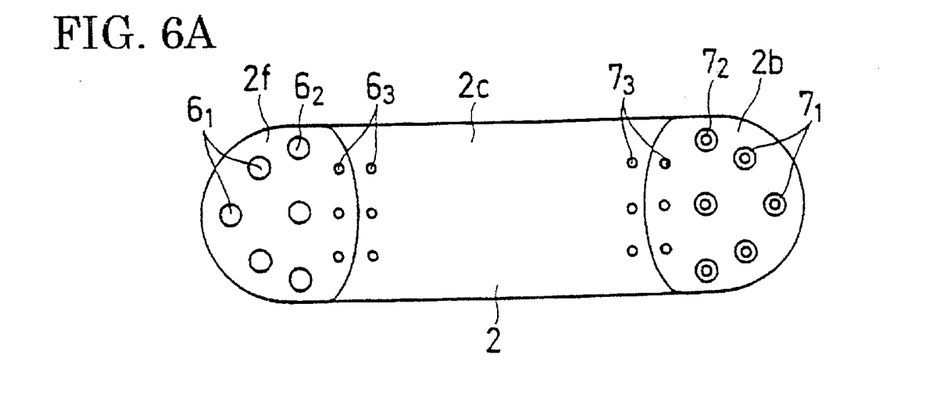
FIG. 6A is a plan view illustrating an alternative example of an attracting pad.
Figure 6B:
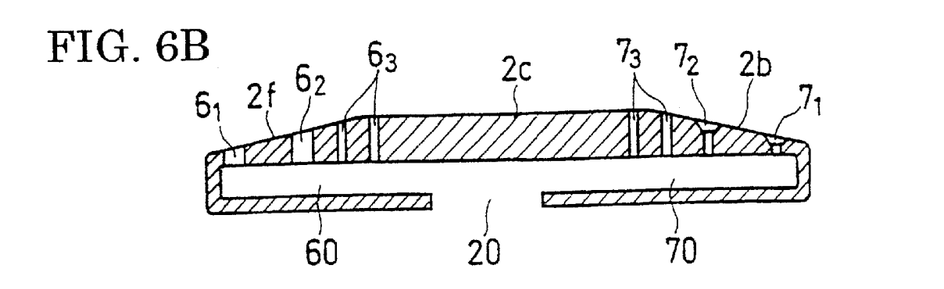
FIG. 6B is a cross-sectional view illustrating the attracting pad of FIG. 6A.

FIG. 6A and FIG. 6B illustrate another example of the attracting pad 2.

As illustrated in these figures, the front attracting section $2f$ and the rear attracting section $2b$ are provided with the same number of suction holes $6_1$ and $7_i$ respectively, having the same opening size. However, the suction holes $7_1$ and $7_2$ of the rear attracting section $2b$ are tapered so as to expand in the vicinity of the opening. Specifically, these suction holes have a greater diameter on the surface of the attracting pad 2 than in other portions thereof that extend into the attracting pad. With the suction holes having such a shape, effects as those of the above-described embodiment can still be obtained because the essential cross-sectional area is small. On the other hand, the front attracting section $2f$ and the rear attracting section $2b$ have substantially the same suction hole opening area, whereby after the worn article N has been completely attracted onto the attracting pad 2, the front attracting section 2f and the rear attracting section 2b can have substantially the same attracting force with substantially the same degree of negative pressure acting thereon. For example, effects as those of the above-described embodiment can be obtained by, for example, designing the attracting pad 2 so that the front attracting section 2f and the rear attracting section 2b have substantially the same suction hole diameter on the surface of the attracting pad 2 while adjusting the diameter of other portions of the suction holes that extend into the attracting pad.

Figure 6C:
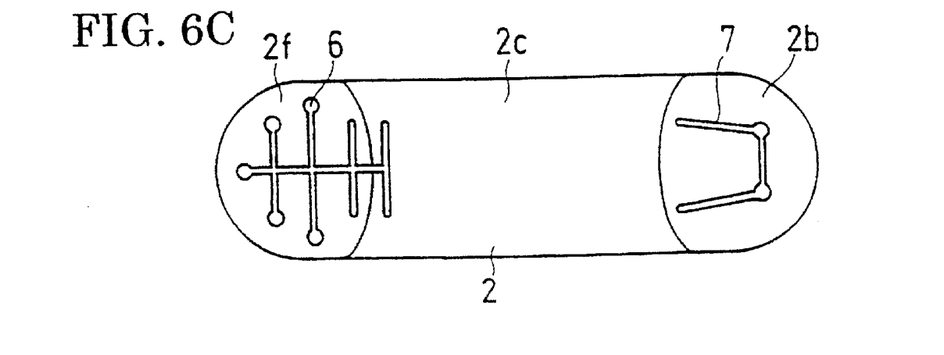
FIG. 6C is a plan view illustrating an alternative example of an attracting pad.

Alternatively, slit-shaped suction holes may be employed as illustrated in FIG. 6C, or a single suction hole having such a shape may be employed. Moreover, the suction holes $6_3$ and $7_3$ of the central portion 2c may also be tapered as the suction holes $7_1$ and $7_2$. While the preferred embodiment of the present invention has been described above with reference to the drawings, it should be understood that various obvious variations and modifications can be readily conceived by those skilled in the art based on the teachings of the present specification.

For example, the central portion 2c may be provided with small suction holes.

Moreover, the air suction path may be provided by making a large number of holes through a deep hole making process and then occluding the holes with a stopper, which may be a resin.

Furthermore, the apparatus in the preceding stage, the transfer apparatus and the apparatus in the subsequent stage may only transfer an article, or may perform a manufacturing step, e.g., a step of processing the article, in addition to transferring the article.

Thus, such variations and modifications shall be interpreted to fall within the scope of the present invention as set forth in the appended claims.

According to the present invention, in the beginning of an article attracting operation, the suction amount through the rear attracting section is reduced, thereby reducing the suction loss, while the suction amount through the front attracting section is increased, thereby improving the reliability of the attraction operation. Then, as the front attracting section is covered by the article, the attracting force of the rear attracting section increases. Therefore, a sufficient attracting force is obtained also in the rear attracting section, thereby improving the reliability of the attraction operation.

What is claimed is:

1. An article transfer apparatus, comprising:
    an attracting pad including a front attracting section and a rear attracting section for attracting an article; and
    a moving section for moving the attracting pad, which is for attracting the article, from a pickup position to a hand-over position, wherein:
        the front attracting section includes at least one suction hole for attracting the article, the suction hole of the front attracting section being communicated to an opening of the attracting pad;
        the rear attracting section includes at least one suction hole for attracting the article, the suction hole of the rear attracting section being communicated to the opening; and
        when a negative pressure is applied on the opening in a non-attracting state, an air suction amount through the suction hole of the front attracting section is greater than an air suction amount through the suction hole of the rear attracting section.

2. An article transfer apparatus according to claim 1, wherein the number of suction holes of the front attracting section is greater than the number of suction holes of the rear attracting section.

3. An article transfer apparatus according to claim 1, wherein a cross-sectional area per unit area of the suction hole in the front attracting section is greater than a cross-sectional area per unit area of the suction hole in the rear attracting section.

4. An article transfer apparatus according to claim 1, wherein:
    the article transfer apparatus comprises a plurality of attracting pads; and
    the moving section moves the attracting pads while changing an interval between the attracting pads.

5. An article transfer apparatus according to claim 1, further comprising an orientation changing section for changing an orientation of the attracting pad while the attracting pad is moved.

6. An article transfer apparatus according to claim 1, wherein the suction hole of the rear attracting section is tapered so as to expand in the vicinity of an opening thereof.

7. A method for manufacturing a disposable worn article, comprising the step of changing an interval between semi-finished products of the disposable worn article by using a transfer apparatus according to claim 1.

8. An article transfer apparatus, comprising:
    an attracting pad including a front attracting section and a rear attracting section for attracting an article; and
    a moving section for moving the attracting pad, which is for attracting the article, from a pickup position to a hand-over position, wherein:
        the front attracting section includes at least one suction hole for attracting the article, the suction hole of the front attracting section being communicated to an opening of the attracting pad;
        the rear attracting section includes at least one suction hole for attracting the article, the suction hole of the rear attracting section being communicated to the opening; and
        when a negative pressure is applied on the opening in a non-attracting state, an air suction resistance through the front attracting section is smaller than an air suction resistance through the rear attracting section.

9. An article transfer apparatus according to claim 8, wherein the number of suction holes of the front attracting section is greater than the number of suction holes of the rear attracting section.

10. An article transfer apparatus according to claim 8, wherein a cross-sectional area per unit area of the suction hole in the front attracting section is greater than a cross-sectional area per unit area of the suction hole in the rear attracting section.

11. An article transfer apparatus according to claim 8, wherein:
    the article transfer apparatus comprises a plurality of attracting pads; and
    the moving section moves the attracting pads while changing an interval between the attracting pads.

12. An article transfer apparatus according to claim 8, further comprising an orientation changing section for changing an orientation of the attracting pad while the attracting pad is moved.

13. An article transfer apparatus according to claim 8, wherein the suction hole of the rear attracting section is tapered so as to expand in the vicinity of an opening thereof.

14. A method for manufacturing a disposable worn article, comprising the step of changing an interval between semi-finished products of the disposable worn article by using a transfer apparatus according to claim 8.

15. An article transfer apparatus, comprising:

an attracting pad including a front attracting section and a rear attracting section for attracting an article; and a moving section for moving the attracting pad, which is for attracting the article, from a pickup position to a hand-over position, wherein:

the front attracting section includes at least one suction hole for attracting the article;

the rear attracting section includes at least one suction hole for attracting the article; and a total cross-sectional area of the suction hole of the front attracting section is greater than a total cross-sectional area of the suction hole of the rear attracting section.

16. An article transfer apparatus according to claim 15, wherein the number of suction holes of the front attracting section is greater than the number of suction holes of the rear attracting section.

17. An article transfer apparatus according to claim 15, wherein a cross-sectional area per unit area of the suction hole in the front attracting section is greater than a cross-sectional area per unit area of the suction hole in the rear attracting section.

18. An article transfer apparatus according to claim 15, wherein:

the article transfer apparatus comprises a plurality of attracting pads; and the moving section moves the attracting pads while changing an interval between the attracting pads.

19. An article transfer apparatus according to claim 15, further comprising an orientation changing section for changing an orientation of the attracting pad while the attracting pad is moved.

20. An article transfer apparatus according to claim 15, wherein the suction hole of the rear attracting section is tapered so as to expand in the vicinity of an opening thereof.

21. A method for manufacturing a disposable worn article, comprising the step of changing an interval between semi-finished products of the disposable worn article by using a transfer apparatus according to claim 15.

* * * * *